United States Patent [19]

Standke et al.

[11] Patent Number: 5,527,937
[45] Date of Patent: Jun. 18, 1996

[54] PROCESS FOR PREPARING HYDROGENALKOXYSILANES

[75] Inventors: Burkhard Standke, Loerrach; Albert Frings, Rheinfelden; Michael Horn, Rheinfelden; Hans-Joachim Koetzsch, Rheinfelden; Frank Kropfgans, Rheinfelden; Jaroslaw Monkiewicz, Rheinfelden; Claus-Dietrich Seiler, Rheinfelden; Hans-Guenther Srebny, Duelmen-Rorup, all of Germany

[73] Assignee: Huels Aktiengesellschaft, Marl, Germany

[21] Appl. No.: 538,636

[22] Filed: Oct. 4, 1995

[30] Foreign Application Priority Data

Oct. 25, 1994 [DE] Germany .................... 44 38 032.1

[51] Int. Cl.$^6$ ..................................... C07F 7/18
[52] U.S. Cl. ........................................... 556/470
[58] Field of Search ................................ 556/470

[56] References Cited

U.S. PATENT DOCUMENTS 3,775,457  11/1973  Muraoka et al. ................ 556/470

FOREIGN PATENT DOCUMENTS

A-0280517  8/1988  European Pat. Off. .
A-0448404  9/1991  European Pat. Off. .
A-2154728  5/1973  France .

OTHER PUBLICATIONS

Wada, H. et al, "Solvent Recycle in Preparation from Silicon and Alcohols", Chemical Abstracts, vol. 109, No. 19, 7 Nov. 1988, p. 741.

*Primary Examiner*—Paul F. Shaver
*Attorney, Agent, or Firm*—Oblon, Spivak, McClelland, Maier & Neustadt

[57] ABSTRACT

Hydrogenalkoxysilanes are prepared by direct reaction of finely divided metallic silicon with alcohols in the presence of copper-containing catalysts in a heat-transfer oil comprising tritoluenes, tetratoluenes or mixtures thereof at from 100° to 350° C.

6 Claims, No Drawings

PROCESS FOR PREPARING HYDROGENALKOXYSILANES

BACKGROUND OF THE INVENTION

1. Field of the Invention

The invention relates to a process for preparing hydrogenalkoxysilanes of formula I

    (I), where n is an integer from 1 to 3 and m can assume the value 0, 1 or 2, by direct reaction of metallic silicon with alcohols in the presence of suitable, copper-containing catalysts.

2. Discussion of the Background

Hydrogenalkoxysilanes are an important group of inorganic silicon compounds. Via the Si—H functional groups, hydrosilylation processes make available organosilanes which can usually only be obtained by esterification of chlorosilanes. Furthermore, monosilanes can be obtained in high purity, for example for semiconductor applications, by base-catalyzed dismutation of hydrogenalkoxysilanes.

It is known that compounds of formula I can be prepared by esterification of the corresponding hydrogenchlorosilanes or, more elegantly, not employing chlorosilanes, by direct reaction of metallic, pulverized silicon with the corresponding alcohols at temperatures above 100° C. using copper-containing catalysts (e.g. U.S. Pat. No. 2,473,260, U.S. Pat. No. 3,641,077, DE 258 961). The industrially and economically most interesting processes use inert heat-transfer oils as reaction media. Here, the copper-containing silicon contact composition is suspended in an inert, liquid medium and is converted into the desired hydrogenalkoxysilane at temperatures above 100° C. by passing a liquid or gaseous alcohol into the reaction medium. The maximum temperature at which this process can be used is determined by the thermal stability of the heat-transfer oil used.

The main byproducts formed in the known direct synthesis are tetraalkoxysilanes and siloxanes. Tetraalkoxysilanes are formed mainly by direct reaction of alcohol with silicon or by reaction of hydrogenalkoxysilanes with alcohol with liberation of hydrogen. Siloxanes are formed mainly by hydrolysis of the alkoxysilanes. The water required for this can originate in dissolved form from the alcohol used or is formed thermally or catalytically by elimination of water from ethanol with formation of ethylene.

In the past, various reaction liquids have been used for the reaction discussed here. On studying the literature, it is conspicuous that the selectivity of the reaction and the utilizability of the silicon used (Si conversion) are dependent on the quality of the inert reaction medium employed. Thus, for example, when silicone oil is used as the reaction medium, a selectivity of 77% is obtained in the preparation of triethoxysilane and only 50% for trimethoxysilane with low total utilization of the Si used (U.S. Pat. No. 3,641,077). This process has been improved by use of alkylbenzenes (EP 0 280 517, U.S. Pat. No. 4,931,578 giving 88.2% selectivity and 81% Si conversion in the synthesis of trimethoxysilane, with the disadvantage that methyl chloride has to be used to activate the contact composition). An oil comprising aromatic hydrocarbons having from 2 to 4 rings and 1<n<4 alkyl groups having less than 4 carbon atoms of formulae $C_{10}H_{8-n}R_n$, $C_{12}H_{10-n}R_n$ [A petroleum cracking product which contains sulphur, which acts as a catalyst poison,] gives 94% selectivity with the disadvantage that hydrogen fluoride has to be used to activate the silicon (DE 2 247 872).

Furthermore, use has been made in the past of the following inert reaction media:

diphenyl oxide (JP 1002693),
isoparaffin mixtures (JP 57108095),
dodecylbenzene (JP 57108094, JP 3027493, JP 3156793),
ditoluenes (JP 54163529),
partially hydrogenated terphenyls (Therminol 59, U.S. Pat. No. 5,084,590, BP 0 462 359).

Although the compounds mentioned are readily available industrially (heat-transfer oils), they do not allow industrially satisfactory values for selectivity and silicon conversion to be obtained. This is the main reason why the process for the direct reaction of metallic silicon with ethanol or methanol has not yet been used on a large industrial scale, although there is an urgent need for this, since the alternative process (esterification of chlorosilanes) is technically complicated. It is furthermore known that the use of certain heat-transfer fluids leads to foaming problems in carrying out the reaction (Comparative Example 3 in DE 2 247 872), which could have catastrophic consequences on a large industrial scale.

A need has therefore continued to exist for reaction media which result in improved conversion of silicon to product while reducing foaming of the reaction mixture.

SUMMARY OF THE INVENTION

Accordingly, one object of the present invention is to provide an improved reaction medium for the reaction of silicon with alcohols in which improved silicon conversions are achieved with reduced foaming.

Briefly, the object and other objects of the present invention as hereinafter will become more readily apparent can be attained in a process of preparing hydrogenalkoxysilanes of formula I:$H_nSi[O(CH_2)_mCH_3]_{4-n}$ wherein n is an integer 1 to 3 and m is 0, 1 or 2, by reacting finely divided silicon with alcohols in a heat transfer oil of tritoluenes, tetratoluenes or mixture thereof in the presence of a copper-containing catalyst.

DETAILED DESCRIPTION OF THE PREFERRED EMBODIMENTS

It has surprisingly been found that tritoluenes and tetratoluenes are more suitable as inert reaction media for the copper-catalyzed reaction of metallic silicon with alcohols to give hydrogenalkoxysilanes than are the substances described in the prior art. Any foaming which occurs, in particular at the end of the reaction, could be readily controlled by addition of small amounts of commercial silicone oils to the reaction media.

The heat-transfer oils employed in the present invention are, if desired substituted, tritoluenes, tetratoluenes or mixtures thereof. Substituents present are, in particular, alkyl groups. Particular preference is given to using a heat-transfer oil comprising a tritoluene isomer mixture having one $CH_3$ group or two $CH_3$ groups per tritoluene molecule and/or a tetratoluene isomer mixture having one or two $CH_3$ groups per tetratoluene molecule.

Tritoluenes and tetratoluenes have an excellent thermal stability and a very good resistance to the substances used and formed in the present process. Silicon powder and catalyst can be very homogeneously dispersed in tritoluene and tetratoluene, so that excellent heat transfer (avoidance of the formation of local superheating because of the exothermicity of the reaction) and a very good catalyst distribution are achieved. The tritoluenes and tetratoluenes have the further advantage that they do not contain the known sulphur and tin catalyst poisons.

On passing ethanol into the hot reaction mixture undesired foaming results, particularly if ethanol vapor is finely atomized and at the end of the reaction, which can lead to the silicon suspension being carried through the column section into the distillate receiver. Surprisingly, this effect can be prevented if a polysiloxane of the structure

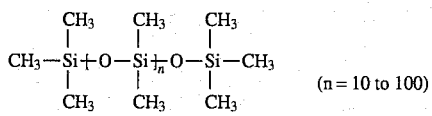

(n = 10 to 100)

is added before foaming occurs. The amount required for this purpose can vary within a wide range (from 0.001 to 5% by weight, based on the total reaction mixture). Normally, the amount ranges from 0.01 to 1% by weight, based on the total reaction mixture, preferably 0.1% by weight.

It is known that pulverulent, anhydrous copper compounds including pulverized, anhydrous copper can be used as catalysts for the reaction under discussion. DE 2247872 refers to the industrially non-problematic availability and good catalytic effectiveness of copper (I) chloride. EP 0 462 359 discloses the use of the copper catalyst in a concentration of from 0.01 to more than 5% by weight. The invention is illustrated below by means of the examples. The examples of the invention were carried out at a temperature of from 100° to 350° C. The alcohols used were methanol or ethanol. The methanol had a purity of more than 98% and a water content of less than 0.1% by weight. The ethanol used was denatured with petroleum ether, had a purity of more than 98% and a water content of less than 0.3% by weight. However, the process of the invention can also be carried out using mixtures of methanol and ethanol and also using other alkanols or alkanol mixtures.

The reactors used for the examples of the invention can be made of copper or glass or can be internally enamelled. The reaction is preferably carried out in glass reactors. Copper(I) chloride in a concentration of from 0.001 to 5% by weight, based on the silicon used, was used as catalyst. The silicon powder was a commercial product having a mean particle size of 75 μm. Commercial dimethylpolysiloxane having a molecular weight of from 162 to 74,000 was employed as an antifoaming agent.

A temperature-controllable stirred reactor of glass having a volume of 500 ml, equipped with alcohol inlet via an immersion tube, temperature control facility, nitrogen blanketing and a distillation apparatus comprising a 20 cm column section (packing: ceramic saddles), condenser and distillate receiver, was charged with heat-transfer oil, silicone oil, catalyst powder and silicon powder, and the contents were heated to 250° C. while stirring. After reaching the set temperature, alcohol was fed in at a metering rate of about 5 ml/min for a period of 4 hours via a metering pump. After the reaction was complete, the alcohol feed was interrupted, and the weight and composition of the distillate were determined.

The composition of the reaction product (distillate) was determined by calibrated, quantitative gas-chromatographic analysis. The silicon conversion was found by gravimetric determination of the residual amount of silicon in the reactor after the reaction was complete.

In the following examples, 30 g of silicon powder, 250 g of heat-transfer oil, 0.6 g of copper(I) chloride and 0.06 g of methylsilicone oil were used in each case.

Example 1

Preparation of triethoxysilane using a tritoluene isomer mixture as heat-transfer oil The yield of triethoxysilane was 87%, the selectivity was 95%, the silicon conversion was 92% and the maximum concentration of triethoxysilane was 30%.

Example 1a (Comparative Example)

The example was carried out as described in Example 1, but without using an antifoaming agent. The ethanol metering rate had to be throttled back to about 70%, since otherwise the reaction mixture foamed into the column section.

| | |
|---|---|
| Yield of triethoxysilane = | 75% |
| Selectivity = | 95% |
| Silicon conversion = | 79% |
| Maximum concentration of triethoxysilane = | 25% |

Example 2

Preparation of trimethoxysilane using a tritoluene isomer mixture as heat-transfer oil

| | |
|---|---|
| Yield of trimethoxysilane = | 85% |
| Selectivity = | 91% |
| Silicon conversion = | 93% |
| Maximum concentration of trimethoxysilane = | 28% |

Example 3

Preparation of triethoxysilane using a tetratoluene isomer mixture as heat-transfer oil

| | |
|---|---|
| Yield of triethoxysilane = | 70% |
| Selectivity = | 83% |
| Silicon conversion = | 84% |
| Maximum concentration of triethoxysilane = | 20% |

Example 4 (Comparative Example)

Preparation of triethoxysilane using dodecylbenzene having a strongly branched alkyl chain (commercial product ILEXAN from HÜLS AG) as heat-transfer oil

| | |
|---|---|
| Yield of triethoxysilane = | 37% |
| Selectivity = | 78% |
| Silicon conversion = | 47% |
| Maximum concentration of triethoxysilane = | 14% |

Example 5 (Comparative Example)

Preparation of triethoxysilane using dodecylbenzene (commercial product of MERCK) as heat-transfer oil

| | |
|---|---|
| Yield of triethoxysilane = | 37% |
| Selectivity = | 91% |
| Silicon conversion = | 41% |
| Maximum concentration of triethoxysilane = | 8% |

Example 6 (Comparative Example)

Preparation of triethoxysilane using terphenyl partially hydrogenated to a degree of about 50% (commercial product SANTOTHERM 66 from MONSANTO) as heat-transfer oil

| | |
|---|---|
| Yield of triethoxysilane = | 69% |
| Selectivity = | 91% |
| Silicon conversion = | 76% |
| Maximum concentration of triethoxysilane = | 18% |

Example 7 (Comparative Example)

Preparation of triethoxysilane using a biphenyl alkylated with one ethyl group (commercial product THERM S 600 from NIPPON STEEL) as heat-transfer oil

| | |
|---|---|
| Yield of triethoxysilane = | 54% |
| Selectivity = | 92% |
| Silicon conversion = | 59% |
| Maximum concentration of triethoxysilane = | 14% |

Example 8 (Comparative Example)

Preparation of triethoxysilane using a mixture of ditolyl ether isomers (commercial product DIPHYL DT from BAYER AG) as heat-transfer oil Strong foaming occurred and this could not be controlled even by addition of silicone oil. Isolation of the target product was not possible.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing hydrogenalkoxysilanes of formula I $$H_nSi[O(CH_2)_mCH_3]_{4-n} \qquad (I),$$

where n is an integer from 1 to 3 and m can assume the value 0, 1 or 2, comprising:

reacting metallic silicon with alcohols or alcohol mixtures in the presence of a copper-containing catalyst, the metallic silicon being in finely divided form in a heat-transfer oil comprising tritoluenes, tetratoluenes or mixtures thereof, optionally substituted, at a temperature of from 100° to 350° C.

2. The process according to claim 1, wherein said alcohol used is methanol, ethanol, or mixtures thereof.

3. The process according to claim 1, wherein the reaction is carried out in the presence of an antifoaming agent of an organopolysiloxane.

4. The process according to claim 3, wherein the antifoaming agent is a methylsilicone oil having a molecular weight of from 162 to 74,000.

5. The process according to claim 1, wherein the catalyst is copper(I) chloride in a concentration of from 0.001 to 5% by weight, based on the silicon.

6. The process according to claim 1, wherein the methylsilicone oil is present in an amount of 0.01 to 1% by wt, based on the total reaction mixture.

* * * * *